United States Patent [19]

Mikhail

[11] 4,209,505
[45] Jun. 24, 1980

[54] PILOCARPINE MOUTHWASH FOR DRY MOUTH RELIEF

[76] Inventor: Adib R. Mikhail, 34 Leisure La., Woodlands, Tex. 77380

[21] Appl. No.: 26,581

[22] Filed: Apr. 3, 1979

[51] Int. Cl.$^2$ .................... A61K 7/22; A61K 31/415
[52] U.S. Cl. ................................ 424/54; 424/273 R
[58] Field of Search .................................. 424/49–58, 424/273 R

[56] References Cited

PUBLICATIONS

Rosenthal "Mouthwashes", Chapter 16, pp. 361–379, in Sagarin et al., Cosmetics Science & Technology, John Wiley Interscience, N.Y., N.Y. 1957.

"Pilocarpine", in Chem. Abstracts 1907–1976, vol. 1–85.

Furstenberg, Trans. Am. Laryng. Rhin. Otol. Soc., pp. 48–54, Jun. 1944.

*Primary Examiner*—Shep K. Rose
*Attorney, Agent, or Firm*—Pravel, Gambrell, Hewitt, Kirk, Kimball & Dodge

[57] ABSTRACT

A composition and method of using same for the treatment of patients suffering from a dry mouth condition, comprising from about 0.025 to about 1.0% by weight pilocarpine pilocarpine nitrate or pilocarpine hydrochloirde, in a sweetened mouthwash carrier. Long lasting relief from the dry mouth condition is obtained by gargling with said pilocarpine mouthwash once or twice daily.

5 Claims, No Drawings

PILOCARPINE MOUTHWASH FOR DRY MOUTH RELIEF

BACKGROUND

This invention relates to a composition of matter and method of using same which produces long lasting relief for patients suffering from a dry mouth condition.

Pilocarpine, as a free base, occurs as a colorless crystals with a melting point of 34° C., and is soluble in water and ethyl alcohol. Pilocarpine and its nitrate and hydrochlorides salts, pilocarpine nitrate and pilocarpine hydrochloride, have long been known as parasympathetic alkaloids. Ingestion of pilocarpine or its salts causes stimulation of the GI track (reflected by an increase in GI motility) and stimulation of various glands, such as salivary glands, pancreas and mucosal cells in the respiratory track. Pilocarpine can also cause diaphoresis. Its internal administration may cause increased peristalsis of the intestines, intense bronchial spasms, accelerated heart and pulse rate, increased secretion by the stomach, increased bronchial secretions, and, if incautiously used, may cause pulmonary edema.

Pilocarpine has been used in internal medicine chiefly as a sudorific to evacuate dropsies or to eliminate toxic substances through the skin. It has been employed internally in the treatment of pruritus, to overcome the retention of urine which frequently occurs after pelvic operations and to induce sweating as a treatment for retrobulbar neuritis. When used as an internal medication it is generally administered as a hypodermic injection.

Today the principal use of pilocarpine is as a local remedy by opthalmologists as a myotic in a 0.5 to 8% solution for the treatment of glaucoma.

Furstenberg, *Trans. Am. Laryng. Rhin. Otol. Soc.*, June 1944, pp. 48–54, disclosed that the oral administration of pilocarpine hydrochloride or pilocarpine nitrate in 10 milligram dosages three times a day temporarily restored salivation in patients suffering from dry mouth. It is apparent from Furstenberg that the remedial effect of the oral ingestion of pilocarpine alone is of very short duration. Thus, Furstenberg disclosed that to increase the longivity of the pilocarpine induced salivation, it is important to prepare the patient for maximum utilization and effectiveness of the drug. In the Furstenberg method the patient is placed in a mild state of acidosis by placing him on an alkali restricted diet and administering three grams of ammonium chloride with meals on a three-dayon and two-day-off basis. Such a diet caused an increase in the acidity of the body tissues which operated to extend the therapeutic action of the pilocarpine.

The Furstenberg method of treating dry mouth condition suffers from certain disadvantages in that: ingestion of pilocarpine may also produces undesirable systemic side effects such as increased sweating, constriction of the pupils, increased heart rate, increased secretion by the stomach, and increased bronchial secretions; and, to obtain prolonged relief the patient is required to follow a restricted diet.

SUMMARY OF THE INVENTION

It has now been found that pilocarpine, as a free base or as a salt, may be nondigestively administered as a topical application in the form of a diluted solution to the mucosa lining of the mouth of patients suffering from a dry mouth condition to produce a long acting relief from such condition without inducing undesirable systemic side effects. Additionally, long acting relief may be obtained without placing any special dieting restrictions upon the patient. Pilocarpine hydrochloride, as a dilute solution of about 0.025 to about 1.0% by weight in a mouthwash carrier is effective when gargled to produce long acting relief from the dry mouth condition. Such pilocarpine mouthwash is especially effective in providing relief to patients suffering from drug induced dry mouth resulting from their treatment with antidepressant, antipsychotic, antihypersensitive and antiallergenic medications.

DETAILED DESCRIPTION OF THE PREFERRED EMBODIMENTS

The mouthwash of the present invention comprises a dilute solution of pilocarpine as a free base, pilocarpine nitrate or pilocarpine hydrochloride. Any liquid in which pilocarpine or its nitrate and hydrochloride salts will dissolve and which is safe for human use may serve as the mouthwash carrier. Since pilocarpine and its salts are bitter in taste it is preferred to use a sweetened mouthwash carrier in order to mask the bitter taste.

Water or ethyl alcohol may be used as the mouthwash carrier. Preferably a sweetening agent such as saccahrin or the like is added to the carrier in amount sufficient to mask the bitter taste. Although water or ethyl alcohol may be used as the carrier, it is preferred to use commercially available over the counter mouthwash compositions as the mouthwash carrier. Any commercially available mouthwash solution in which pilocarpine, pilocarpine nitrate or pilocarpine hydrochloride are soluble may be used as the mouthwash carrier in this invention. It is preferred to use a commercially available mouthwash since, in addition to being a suitable carrier for pilocarpine or its salts, such carriers are generally effective in masking the bitter taste while simultaneously they stimulate and refresh the patient's mouth and therefore further enhances the relief attainable from the unpleasant dry mouth condition. Commercial mouthwash solutions typically comprise a water-alcohol based solution containing additional components such a glycerine, saccharine, citric acid, clove oil, flavors and food colorings. The particular composition of the commercial mouthwash is not important to the operability of the invention as providing long lasting relief from dry mouth, the only restriction on selection being that the mouthwash carrier chosen be capable of dissolving small amounts of pilocarpine or its nitrate and hydrochloride salts. Of the mouthwash solutions employed LAVORIS has so far been found to be the most effective commercial mouthwash carrier for masking the bitter taste of pilocarpine and its salts. LAVORIS, as disclosed by its label, contains; water, SD alcohol 38-B, glycerin, poloxamer 407, saccharin, polysorbate 80, zinc chloride, flavors, citric acid, clove oil, and food coloring.

The pilocarpine mouthwash compositions of the present invention are made by dissolving from about 0.025 percent by weight or greater amounts of pilocarpine, pilocarpine nitrate or pilocarpine hydrochloride in the mouthwash carrier. Any amount of pilocarpine greater than about 0.025 percent by weight when dissolved in a mouthwash carrier is effective, when gargled, in providing long acting relief from the dry mouth condition. Although pilocarpine or its nitrate or hydrochloride salts may be employed in amounts greater than 1 percent by weight of the total solution, such higher concentrations do not add measurably to the longivity of relief from the dry mouth condition. Since pilocarpine, pilocarpine nitrate and pilocarpine hydrochloride are bitter to the taste it is preferred to employ these bitter agents in the minimum amounts necessary to affect relief from dry mouth. It is preferred to employ the pilocarpine or its salts in amounts which range from about 0.05 percent to about 1.0 percent by weight of the mouthwash carrier.

The preferred form of pilocarpine for use in this invention is pilocarpine hydrochloride since it is soluble in common water-alcohol based commercial mouth wash solutions to a greater degree than is pilocarpine or pilocarpine nitrate.

The above described pilocarpine mouthwash is applied topically in a non-digestive treatment to the mucosal lining of the mouth of patients suffering from dry mouth to provide long lasting relief from such condition. The most effective mode of application is to have the patient gargle with the pilocarpine mouthwash for about 30 seconds or longer, the mouthwash thereafter being expelled from the mouth. The number of applications per day will vary somewhat depending upon the particular patient involved. Generally it has been found that a patient need only gargle with the pilocarpine mouthwash about once to twice a day. In some cases, again depending upon the particular patient, it has been found that one application every other day provides relief from the dry mouth condition.

The pilocarpine mouthwash has been found especially effective in relieving dry mouth associated with the use of antihypertensive, antidepressant, antipsychotic, and antiallergetic medications which induce dry mouth. Examples of antidepressants which induce dry mouth and for which the mouthwash of the present invention is effective for relief include Elavil, Tofranil, Vivactil, Sinequan, Limbitrol and Aventyl. Examples of antipsychotic medications for which the pilocarpine mouthwash has been found to be effective in relieving dry mouth include Thorazine, Mellaril, Serentil, Haldol, Prolixin, Stelazine, and Navane.

L-Dopa derivatives which are used in the treatment of Parkinsonism also induce dry mouth which may be alleviated by gargling with the pilocarpine mouthwash of the present invention. Dry mouth may also be caused by radiotherapy and renal dialysis, and when such condition occurs it may be effectively treated with the pilocarpine mouthwash.

Gargling with a mouthwash solution containing one percent pilocarpine hydrochloride has been found to be effective in providing relief from dry mouth for from about six to about eight hours per application. The long acting relief obtainable by gargling with a pilocarpine mouthwash does not depend upon any special patient preconditioning.

An additional advantage of the application of pilocarpine as a topical mouthwash application which is expelled from the mouth after treatment, as compared to prior ingestive techniques, is that it may be used to alleviate the dry mouth condition without, at the same time, inducing any adverse systemic side effects such a increased heart rate, increased sweating and increased gastric motility and the like normally associated with the internal administration of pilocarpine or its salts.

To date, about forty patients suffering from drug induced dry mouth have been treated with a pilocarpine hydrochloride mouthwash as described above. These patients have been undergoing treatment with various antidepressant, antipsychotic and antihypertensive medications. Such patients were advised to gargle with the mouthwash as needed and to expel the solution from their mouth upon completion of gargling. In each case the patient reported that gargling with a pilocarpine hydrochloride mouthwash provided relief from the dry mouth condition ranging, on an average, from about six to about eight hours. The number of treatments required to provide continual relief varied from a low of one application every other day to about two applications per day. No patient complained of any adverse systemic side effects and none were observed.

Although the invention has been described in reference to its preferred embodiments those of ordinary skill in the art may make modifications therein without departing from the scope and spirit of the invention which is claimed as follows.

1. A method of treating a patient suffering from dry mouth, comprising the step of:
   contacting the mucosal lining of the mouth of said patient, without ingestion, with a liquid carrier containing at least about 0.025 percent by weight of pilocarpine, pilocarpine nitrate or pilocarpine hydrochloride.

2. The method of claim 1, wherein said liquid carrier comprises a water-alcohol solution.

3. The method claim 1, wherein said liquid carrier contains a sweeting agent.

4. The method of claim 3, wherein said liquid carrier contains from about 0.025 to 1 percent pilocarpine hydrochloride.

5. The method of claim 1, wherein the duration of said contact is at least about 30 seconds.

* * * * *

UNITED STATES PATENT AND TRADEMARK OFFICE
CERTIFICATE OF CORRECTION

PATENT NO. : 4,209,505

DATED : June 24, 1980

INVENTOR(S) : Adib R. Mikhail

It is certified that error appears in the above-identified patent and that said Letters Patent are hereby corrected as shown below:

Title Page, Under "Abstract", line 5, please cancel "chloirde" and insert --chloride--.

Column 1, line 44, please cancel "longivity" and insert --longevity--.

Column 1, line 50, please cancel "three-dayon" and insert --three-day-on--.

Column 2, line 27, please cancel "saccahrin" and insert --saccharin--.

Column 3, line 2, please cancel "longivity" and insert --longevity--.

Column 3, line 34, please cancel "antiallergetic" and insert --anti-allergenic--.

Column 4, line 46, please cancel "sweeting" and insert --sweetening--.

Signed and Sealed this

Second Day of December 198

[SEAL]

Attest:

SIDNEY A. DIAMOND

Attesting Officer

Commissioner of Patents and Trademar